United States Patent
Chung et al.

(10) Patent No.: US 11,366,065 B2
(45) Date of Patent: Jun. 21, 2022

(54) POINT-OF-CARE SYSTEM AND METHOD FOR DIAGNOSING ACUTE FEBRILE ILLNESS

(71) Applicants: SAMSUNG LIFE PUBLIC WELFARE FOUNDATION, Seoul (KR); INDUSTRY-UNIVERSITY COOPERATION FOUNDATION HANYANG UNIVERSITY ERICA CAMPUS, Ansan-si (KR)

(72) Inventors: Doo Ryeon Chung, Seoul (KR); Min Hee Kang, Seoul (KR); Nam Yong Lee, Seoul (KR); Min Young Lee, Seoul (KR); Kyu Sung Lee, Seoul (KR); Jae Bum Choo, Ansan-si (KR); Sang Yeop Lee, Ansan-si (KR); Joon Ki Hwang, Gangneung-si (KR)

(73) Assignees: SAMSUNG LIFE PUBLIC WELFARE FOUNDATION; INDUSTRY-UNIVERSITY COOPERATION FOUNDATION HANYANG UNIVERSITY, ERICA CAMPUS

( * ) Notice: Subject to any disclaimer, the term of this patent is extended or adjusted under 35 U.S.C. 154(b) by 362 days.

(21) Appl. No.: 16/483,195

(22) PCT Filed: Feb. 1, 2018

(86) PCT No.: PCT/KR2018/001369
§ 371 (c)(1),
(2) Date: Aug. 2, 2019

(87) PCT Pub. No.: WO2018/143684
PCT Pub. Date: Aug. 9, 2018

(65) Prior Publication Data
US 2019/0369026 A1    Dec. 5, 2019

(30) Foreign Application Priority Data

Feb. 3, 2017 (KR) .................... 10-2017-0015390
Feb. 1, 2018 (KR) .................... 10-2018-0012663

(51) Int. Cl.
*G01N 21/65* (2006.01)
*G01N 33/49* (2006.01)
(Continued)

(52) U.S. Cl.
CPC .......... *G01N 21/658* (2013.01); *G01N 33/49* (2013.01); *G01N 33/54346* (2013.01); *G01N 33/6893* (2013.01); *G01N 2800/26* (2013.01)

(58) Field of Classification Search
CPC .. G01N 21/658; G01N 21/65; G01N 2800/26; G01N 33/49; G01N 33/54346;
(Continued)

(56) References Cited

U.S. PATENT DOCUMENTS

| 2007/0031283 A1* | 2/2007 | Davis ............... A61B 5/150221 422/400 |
| 2013/0287772 A1 | 10/2013 | Halbert et al. |
| 2018/0217068 A1* | 8/2018 | Tabb .................... C12N 15/115 |

FOREIGN PATENT DOCUMENTS

| CN | 105548178 A | 5/2016 |
| CN | 105603125 A | 5/2016 |

(Continued)

OTHER PUBLICATIONS

Jeong Jin Ha et al., May 3, 2016, Machine English Translation of Description of Korean Patent Application KR 20160047890, Espacenet (Year: 2016).*

(Continued)

*Primary Examiner* — Christine T Mui
*Assistant Examiner* — Kathryn Elizabeth Limbaugh
(74) *Attorney, Agent, or Firm* — Myers Bigel, P.A.

(57) ABSTRACT

Disclosed are a point-of-care system and method, the system including: an aptamer-based diagnostic reagent; a diagnostic instrument for detecting a Raman signal through a Raman analysis technique; and a diagnostic kit to be operated on the basis of a lateral flow method, wherein blood and the diagnostic reagent are reacted so as to detect a Raman signal when the placement of the diagnostic kit is detected, thereby allowing the type of acute febrile illness to be identified.

12 Claims, 8 Drawing Sheets

(51) Int. Cl.
*G01N 33/543* (2006.01)
*G01N 33/68* (2006.01)
(58) Field of Classification Search
CPC .. G01N 2800/6893; A61B 5/00; A61B 5/0075
See application file for complete search history.

(56) References Cited

FOREIGN PATENT DOCUMENTS

| | | |
|---|---|---|
| JP | 2016029400 | 3/2016 |
| KR | 20110019843 | 3/2011 |
| KR | 20150104076 | 9/2015 |
| KR | 20160047890 | 5/2016 |
| WO | 2011/021896 | 2/2011 |
| WO | 2016/134214 | 8/2016 |

OTHER PUBLICATIONS

Espacenet English Translation of CN105548178. (Year: 2016).*
International Search Report corresponding to International Application No. PCT/KR2018/001369, dated May 14, 2018 (5 pages with English translation).
Food Microbiology Laboratory, edited by Lynne Mclandsborough, China Light Industry Press, published in April of 2007, 3 pages, no translation.

* cited by examiner

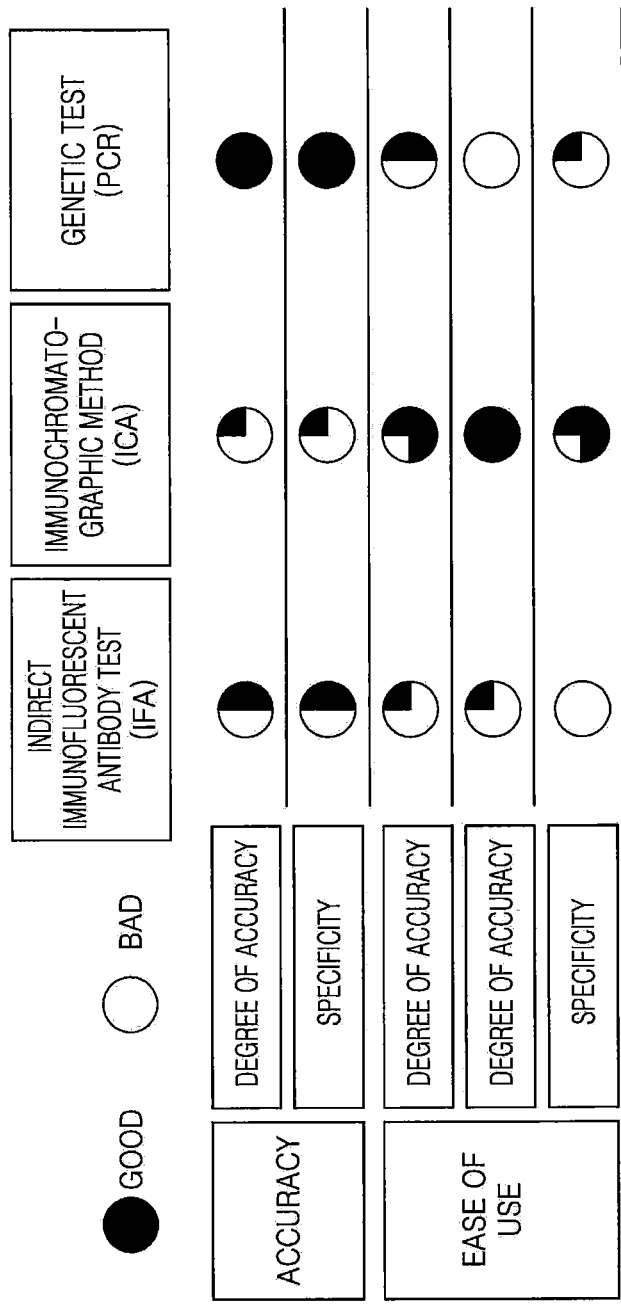

(a)     (b)

POINT-OF-CARE SYSTEM AND METHOD FOR DIAGNOSING ACUTE FEBRILE ILLNESS

CROSS REFERENCE TO RELATED APPLICATIONS

This application is a 35 U.S.C. § 371 national stage application of PCT International Application No. PCT/KR2018/001369, filed Feb. 1, 2018, which claims priority from Korean Patent Application Nos. 10-2018-0012663 and 10-2017-0015390, filed Feb. 1, 2018 and Feb. 3, 2017, respectively, the contents of which are incorporated herein in their entireties by reference. The above-referenced PCT International Application was published in the Korean language as International Publication No. WO 2018/143684 A1 on Aug. 9, 2018.

TECHNICAL FIELD

The present invention relates to a system and a method for diagnosing an acute febrile illness, and more particularly, to a system and a method for accurately and rapidly diagnosing various types of autumn acute febrile illness.

BACKGROUND ART

A representative acute febrile illness which spreads in an autumn season includes tsutsugamushi, leptospirosis, rash fever, and hemorrhagic fever of nephrotic syndrome. Common symptoms of the illnesses involving an illness such as a bad cold and flu while running a fever. The autumn acute febrile illnesses may lead to complications, and in serious cases, a patient dies, and as a result, it is important for the patient to receive appropriate treatment soon.

Meanwhile, a frequency of the acute febrile illnesses that spread in autumn has increased rapidly in recent years. However, even though early symptoms of the diseases are similar to each other and it is not easy to distinguish the early symptoms early, there is a difference between the treatment and a prognosis of each illness, so accurate identification is very important.

DETAILED DESCRIPTION OF THE INVENTION

Technical Problem

The present invention is contrived to solve such a problem and an object of the present invention is to improve efficiency of field diagnosis by accurately and rapidly determining various accurate febrile illnesses.

Another object of the present invention is to guarantee accessibility to a diagnosis method by minimizing an increase in diagnosis cost and lowering an expertise required for the diagnosis while improving efficiency of the field diagnosis.

The technical objects to be achieved by the present invention are not limited to the aforementioned technical objects, and other technical objects, which are not mentioned above, may be considered by those skilled in the art from embodiments of the present invention to be described below.

Technical Solution

In order to solve the technical problem, a point-of-care system includes: a diagnostic reagent detecting target antigens based on an aptamer; a diagnostic instrument detecting a Raman signal through a Raman analysis technique; and a diagnostic kit seated on the diagnostic instrument and operated based on a lateral flow method, in which the diagnostic instrument includes a diagnostic kit seating unit detecting that the diagnostic kit is placed, a Raman analysis execution unit reacting a blood injected into the diagnostic kit and the diagnostic reagent to each other when the diagnostic kit is placed and amplifying and detecting a generated Raman signal, an illness analysis unit analyzing the type of acute febrile illness infected by a subject according to the detected Raman signal, and an output unit outputting information on the analyzed illness.

The diagnostic reagent may include aptamer for antigen detection and fixed aptamer and directly detect antigen in the blood injected into the diagnostic kit.

The diagnostic kit seating unit may include at least one of a pressure sensor, an optical sensor, and an electrical signal transmitting and receiving means for detecting that the diagnostic kit is placed.

The Raman analysis execution unit may amplify and detect the Raman signal by using a Surface Enhanced Raman Scattering (SERS) technique and gold-silver nanoparticles.

The output unit may include a display unit for visually providing information on the illness and a speaker for audibly providing the information.

In order to solve the technical problem, a point-of-care method includes: detecting, by the diagnostic instrument detecting a Raman signal through a Raman analysis technique, that the diagnostic kit operated by a lateral flow method is placed; when it is detected that the diagnostic kit is placed, detecting the Raman signal generated by reacting a blood injected into the diagnostic kit and the aptamer-based diagnostic reagent; detecting an antigen through an analysis process of the Raman signal; checking the type of acute febrile illness infected by a subject according to the detected antigen; and outputting information on the analyzed illness.

Advantageous Effects

According to embodiments of the present invention, the following effects can be expected.

First, despite similar early symptoms of acute febrile illnesses that spread in the autumn, it is possible to accurately distinguish illnesses, thereby minimizing the risk of misdiagnosis and complications.

Second, since it is possible to accurately differentiate a variety of illnesses, the risk of antibiotic resistance can be minimized, which can be caused by the treatment of allopathic antibiotics, which rely on empirical treatment.

Third, accurate diagnosis and rapid diagnosis are possible, and as a result, time constraints and space constraints of Point of Care Testing (POCT) can be eliminated.

Effects which can be obtained in embodiments of the present invention are not limited to the aforementioned effects and other unmentioned effects may be clearly derived and understood by those skilled in the art from a description for embodiments of the present invention to be described below. In other words, undesirable effects according to implementing the present invention can also be derived by those skilled in the art from the embodiments of the present invention.

BRIEF DESCRIPTION OF DRAWINGS

The accompanying drawings, which are to provide a further understanding of the present invention, provide embodiments of the present invention together with the detailed description. It is to be understood, however, that technical features of the present invention are not limited to specific drawings and features disclosed in the respective drawings may be combined with each other to constitute a new embodiment.

FIG. 1a is a diagram illustrating autumn acute febrile illness diagnosis methods in the related art related to a proposed embodiment.

BEST MODE

Figure 1B:
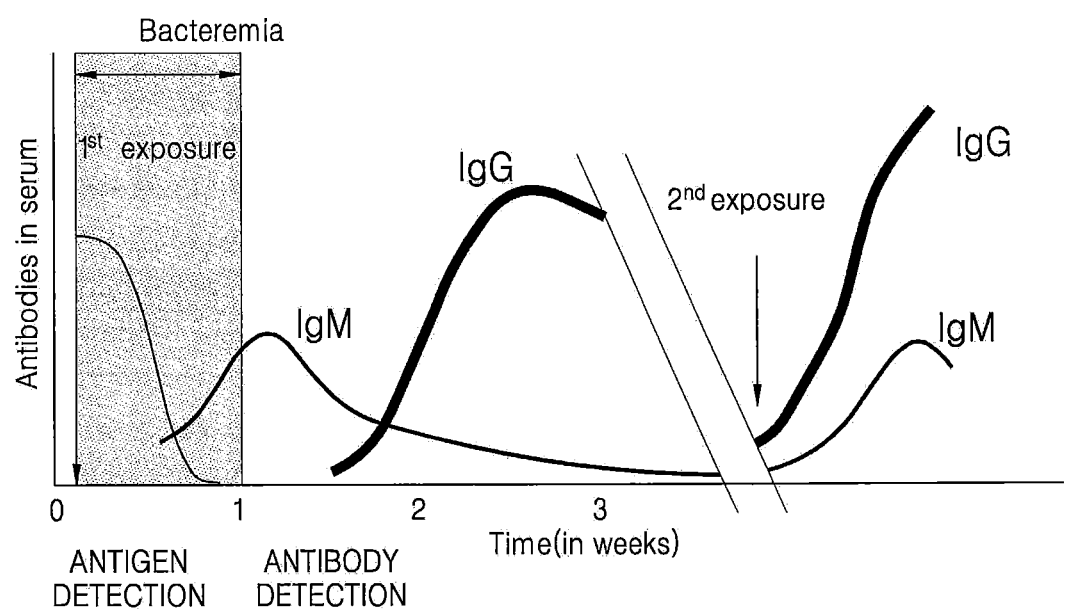
FIG. 1b is a diagram illustrating changes in concentration of IgM and IgG in serum according to an examination time.

In order to solve the technical problem, a point-of-care system includes: a diagnostic reagent detecting target antigens based on an aptamer; a diagnostic instrument detecting a Raman signal through a Raman analysis technique; and a diagnostic kit seated on the diagnostic instrument and operated based on a lateral flow method, in which the diagnostic instrument includes a diagnostic kit seating unit detecting that the diagnostic kit is placed, a Raman analysis execution unit reacting a blood injected into the diagnostic kit and the diagnostic reagent to each other when the diagnostic kit is placed and amplifying and detecting a generated Raman signal, an illness analysis unit analyzing the type of acute febrile illness infected by a subject according to the detected Raman signal, and an output unit outputting information on the analyzed illness.

The diagnostic reagent may include an aptamer for antigen detection and a fixed aptamer and directly detect an antigen in the blood injected into the diagnostic kit.

The diagnostic kit seating unit may include at least one of a pressure sensor, an optical sensor, and an electrical signal transmitting and receiving means for detecting that the diagnostic kit is placed.

The Raman analysis execution unit may amplify and detect the Raman signal by using a Surface Enhanced Raman Scattering (SERS) technique and gold-silver nanoparticles.

The output unit may include a display unit for visually providing information on the illness and a speaker for audibly providing the information.

In order to solve the technical problem, a point-of-care method includes: detecting, by the diagnostic instrument detecting a Raman signal through a Raman analysis technique, that the diagnostic kit operated by a lateral flow method is placed; when it is detected that the diagnostic kit is placed, detecting the Raman signal generated by reacting a blood injected into the diagnostic kit and the aptamer-based diagnostic reagent; detecting an antigen through an analysis process of the Raman signal; checking the type of acute febrile illness infected by a subject according to the detected antigen; and outputting information on the analyzed illness.

Mode for Invention

Hereinafter, embodiments of the present invention will be described in detail so as to be easily implemented by those skilled in the art, with reference to the accompanying drawings. However, the present invention may be implemented in various different forms and is not limited to an embodiment described herein. In addition, in the drawings, in order to clearly describe the present invention, a part not related to the description is not omitted and like reference numerals designate like elements throughout the specification.

Terms used in the present specification will be described in brief and the present invention will be described in detail.

Terms used in the present invention adopt general terms which are currently widely used as possible by considering functions in the present invention, but the terms may be changed depending on an intention of those skilled in the art, a precedent, emergence of new technology, etc. Further, in a specific case, a term which an applicant arbitrarily selects is present and in this case, a meaning of the term will be disclosed in detail in a corresponding description part of the invention. Accordingly, a term used in the present invention should be defined based on not just a name of the term but a meaning of the term and contents throughout the present invention.

Further, throughout the specification, unless explicitly described to the contrary, the word "comprise" and variations such as "comprises" or "comprising", will be understood to imply the inclusion of stated elements but not the exclusion of any other elements. In addition, terms including "part", "module", and the like disclosed in the specification mean a unit that processes at least one function or operation and this may be implemented by hardware or software or a combination of hardware and software. Further, throughout the specification, when it is described that a part is "connected" with another part, it means that the certain part may be "directly connected" with another part and a third part may be interposed therebetween as well.

Hereinafter, the present invention will be described in detail with reference to the accompanying drawings.

The acute febrile illness of autumn, typified by Tsutsugamushi, rash fever, and leptospirosis, takes at least 5 days to show manifest symptoms through Bacteremia after infection and since the concentrations of IgM and IgG in serum changes with time, diagnosis according to a detection time and a detection target is needed. Conventional indirect immunofluorescent antibody test (IFA) and molecular diagnostics (PCR) are not suitable for rapid diagnosis and in the case of a commercialized rapid diagnostic kit, it is difficult to objectify a quantitative numerical value in evaluating readout errors and antibody titers.

Aptamer-based diagnostic reagents, Raman-based highly sensitive lateral flow diagnostic kits, and small Raman analyzers are techniques that may contribute to improving accuracy or ease of use by complementing the limitations of technology applied to the existing diagnosis field. In other words, the point-of-care system for diagnosing the acute febrile illness according to an embodiment of the present invention may perform concurrent-rapid diagnosis of multiple targets of an antigen, an antibody (IgG, IgM) using a Raman diagnostic reagent and a small Raman analyzer, establish a diagnosis criterion through high-sensitivity and quantitative analysis through amplification technology of a Raman signal, and enhance accuracy of examination.

FIG. 1a is a diagram illustrating autumn acute febrile illness diagnosis methods in the related art related to a proposed embodiment and FIG. 1b is a diagram illustrating changes in concentrations of IgM and IgG in serum according to an examination time.

As the representative autumn acute febrile illness, tsutsugamushi, leptospirosis, rash fever, and hemorrhagic fever of nephrotic syndrome are described as an example. The acute febrile illnesses are increasing in frequency due to the increase of outdoor activity in autumn, and the distribution of the incidence is also increasing due to the national increase of temperature in the autumn.

Initial symptoms of the four typical acute febrile illnesses are similar to those of a bad cold and flu, but the treatment and prognosis of each are different and rapid and accurate diagnosis may be very important.

FIG. 1a shows several diagnostic methods that are currently used to diagnose the autumn acute febrile illness. The indirect immunofluorescent antibody test (IFA), which is commonly used, shows relatively good performance in terms of accuracy of the results, but clinical usefulness is limited in that antibody formed 1 to 2 weeks after occurrence of the illness is used. As another diagnostic method, immunochromatography (ICA) is fast and convenient and may be diagnosed at low cost, but the accuracy and sensitivity of the diagnosis result is relatively low. Last, a polymerase chain reaction (PCR) using the gene ensures the accuracy of the result, but a test sample is limited and a long time is required, and there is a limit in that skilled manpower is required.

In other words, various conventional methods for diagnosing the autumn acute febrile illnesses have parts to be improved in terms of accuracy or easiness. Therefore, a diagnosis system and a diagnosis method capable of implementing a new type of Point of Care Testing (POCT) will be described below by suggesting an embodiment.

Figure 2:
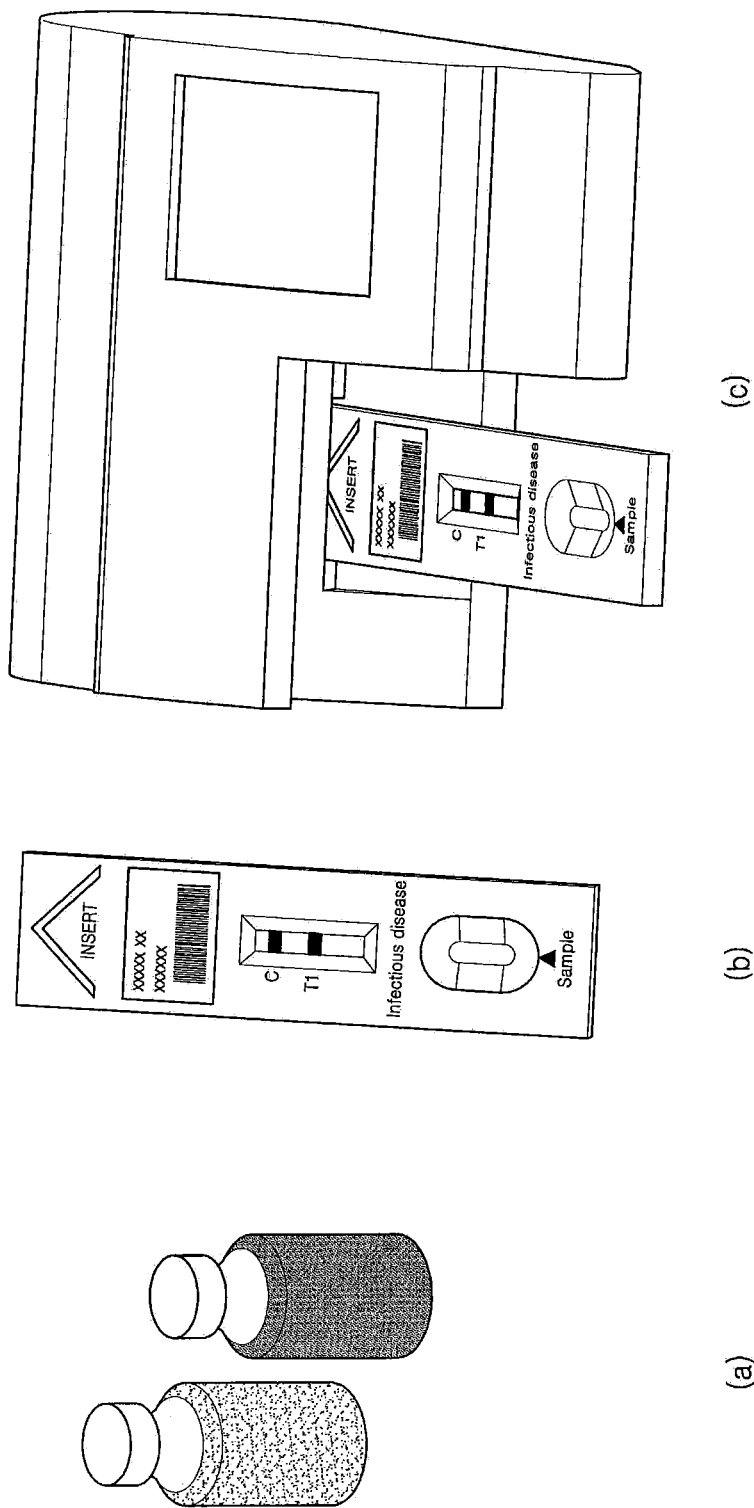
FIG. 2 is a diagram schematically illustrating a point-of-care system according to a proposed embodiment.

FIG. 2 is a diagram schematically illustrating a point-of-care system according to a proposed embodiment. The point-of-care system according to the proposed embodiment is constituted by a diagnostic reagent (FIG. 2(a)), a diagnostic kit (FIG. 2(b)), and a diagnostic equipment (FIG. 2(c)). The illustrated point-of-care system as a system for implementing rapid and accurate diagnosis on a point is implemented to include an aptamer based diagnostic reagent, a Raman analysis based high-sensitivity lateral flow diagnostic kit, and a miniaturized Raman analysis equipment as element technology.

Hereinafter, a configuration of the proposed point-of-care system illustrated in FIG. 2 will be each described in detail.

First, the aptamer is a polymer substance having a property of three-dimensionally binding with a target protein, and the aptamer based diagnostic reagent (FIG. 2(a)) binds to the target antigen with high specificity and affinity. The related art depends on a serological method in order to diagnose autumn illnesses (Tsutsugamushi, leptospirosis, rash fever, hemorrhagic fever with renal syndrome, etc.) and according to the serological method, the pathogen itself may not be detected, and as a result, a time of approximately 3 to 7 days consumed for formation of the antibody is essentially consumed.

On the contrary, in the proposed point-of-care system, according to the aptamer based diagnostic reagent, the pathogen itself (i.e., antigen) may be detected and generation of the antibody need not be waited, and as a result, the illness may be diagnosed in real time as a time for which the generation of the antibody needs to be waited is reduced for diagnosis and analysis of the illness. In other words, the aptamer based diagnostic reagent has the advantage that the antigen in the blood may be directly detected unlike the conventional method of indirectly detecting the antibody for the antigen detection. Therefore, the accuracy and the rapidness of the diagnosis may be ensured through the aptamer based diagnostic reagent. In addition, by applying the aptamer based diagnostic reagent to the Raman analysis technique described below, high specificity diagnosis that minimizes cross-reactivity becomes possible.

Next, the diagnostic kit (FIG. 2(b)) will be described. The proposed diagnostic kit is based on a lateral flow assay analysis technique and the diagnosis kit using the lateral flow may diagnose the illness within a short time even with one two drops of blood, and as a result, the diagnostic kit is very suitable for point diagnosis. Further, the diagnostic kit using the lateral flow analysis technique is advantageous in terms of analysis cost and the skilled manpower is not required.

The lateral flow based diagnostic kit is a method that uses capillary force of paper originating from a high-density volume, a hydrophilic environment, and a micro/nano hole originating from a 3D hierarchical structure of a cellulose fiber network.

Last, the miniaturized Raman analysis based diagnostic equipment (FIG. 2(c)) will be described. The Raman analysis method is suitable as diagnostic equipment for the point because required power is low as compared with the fluorescent diagnostic method. Further, the Raman analysis technique has several tens of times or more higher sensitivity than the existing immunity based diagnostic method, and as a result, a diagnosis result having high sensitivity may be obtained. In particular, the diagnostic equipment is miniaturized to have improved portability, thereby improving the suitability to the POCT.

The point-of-care system constituted by the aptamer based diagnostic reagent, the lateral flow based diagnostic kit, and the Raman analysis based diagnostic equipment enables the acute febrile illness to be diagnosed with high specificity and high sensitivity. In addition, the point-of-care system on-site diagnostic system is very important in terms of specificity and sensitivity as well as rapidity in terms of characteristics thereof and as described above, by integrally using the aptamer based reagent, the lateral flow based diagnostic kit, and the Raman analysis based diagnostic equipment, a diagnostic system utilized timely on the point may be implemented.

Figure 3:
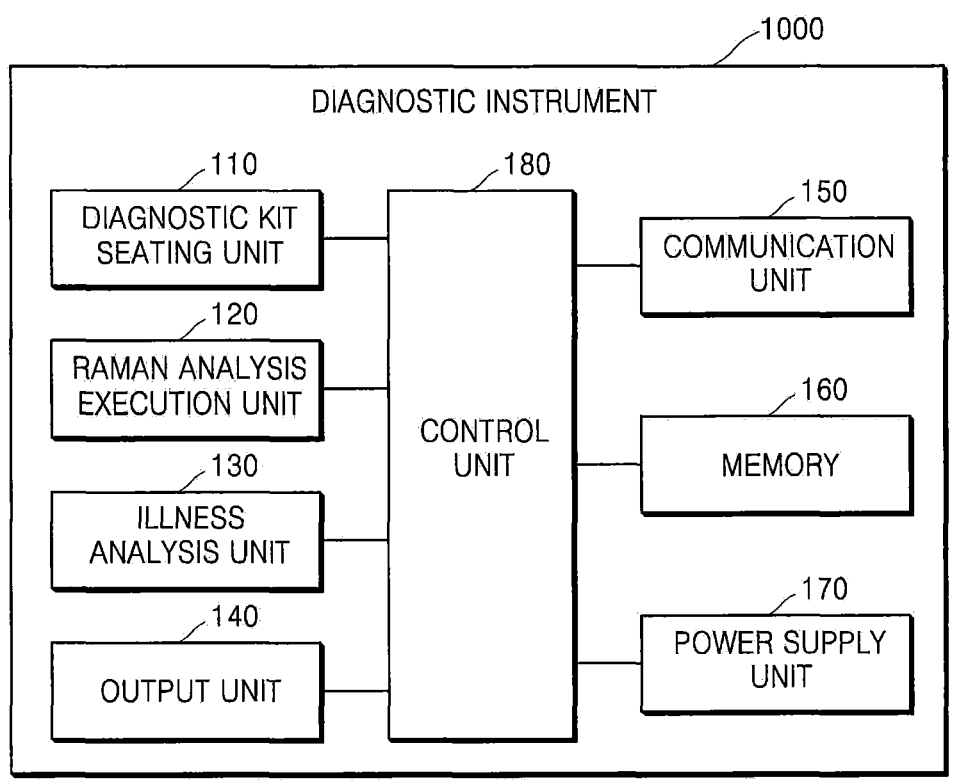
FIG. 3 is a block diagram illustrating a configuration of a diagnostic instrument a point-of-care system according to a proposed embodiment.
Figure 7:
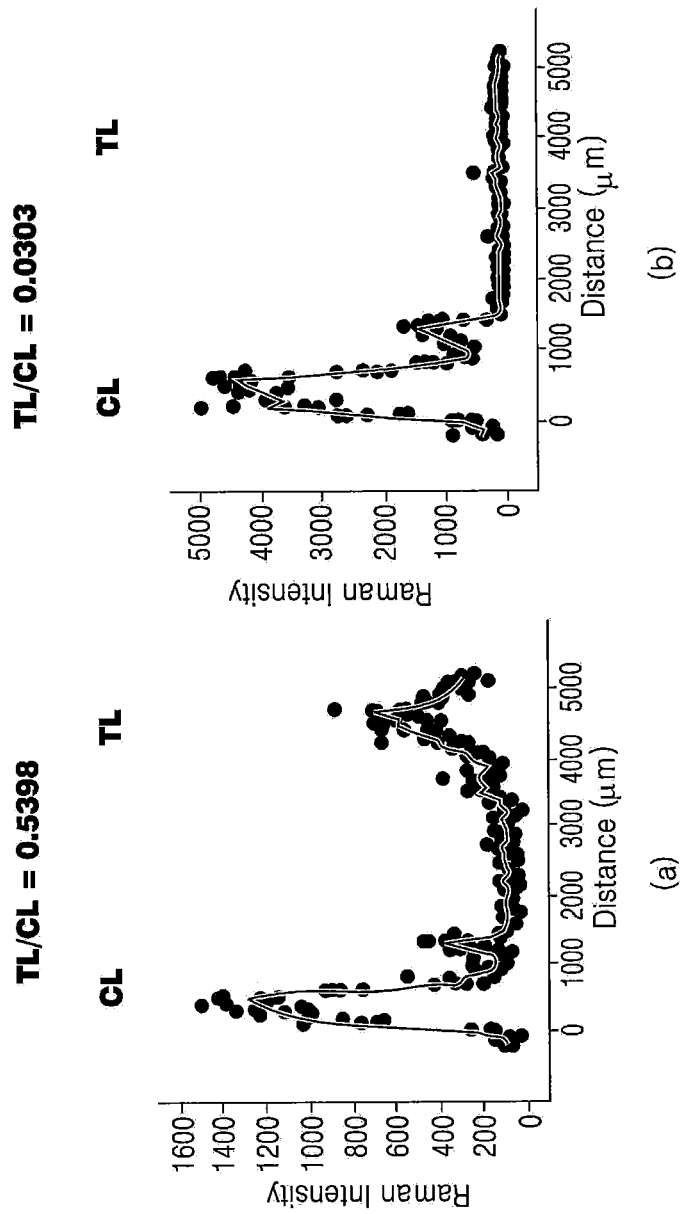
FIG. 7 is a diagram illustrating Raman signal analysis results for (a) positive samples and (b) negative samples.

FIG. 3 is a block diagram illustrating a configuration of a diagnostic instrument a point-of-care system according to a proposed embodiment and FIG. 7 is a diagram illustrating Raman signal analysis results for (a) positive samples and (b) negative samples. In FIG. 3, among the diagnostic reagent, the diagnostic kit, and the diagnostic equipment constituting the proposed point-of-care system, the diagnostic equipment 1000 will be described in detail. The diagnostic equipment 1000 includes a diagnostic kit seating unit 110, a Raman analysis execution unit 120, an illness analysis unit 130, an output unit 140, a communication unit 150, a memory 160, a power supply unit 170, and a control unit 180 illustrated in FIG. 3, but is not limited to such components and may further include other universal components or may be implemented only by fewer components.

The diagnostic kit seating unit 110 as a member in which the diagnostic kit is disposed detects that the diagnostic kit into a blood of a subject is injected is placed on the diagnostic equipment. The diagnostic kit seating unit 110 may detect placement of the diagnostic kit by using a predetermined sensor and for example, a pressure sensor, an optical sensor, and the like may be utilized to detect that the diagnostic kit is placed in the diagnostic equipment 1000. Alternatively, the diagnostic kit seating unit 110 transmits and receives an electrical signal to and from the diagnostic kit to detect that the diagnostic kit is placed.

The Raman analysis execution unit 120 performs Raman analysis for the blood injected into the diagnostic kit as the diagnostic kit seating unit 110 detects that the diagnostic kit is placed. In order to detect a biomarker which exists in the blood through the Raman analysis, a Surface Enhanced Raman Scattering (SERS) technique for amplifying the Raman signal may be applied.

In order to stably acquire the Raman signal formed on a Control (C) line and a Test (T) line of the diagnostic kit, the Raman signal may be acquired by measuring a Raman intensity ratio by polynomial fitting after scanning multiple lines. The scanning may be consecutively performed to the Test (T) line from the Control (C) line.

As illustrated in FIG. 7, signals of a control line (CL) and a test line (TL) of the diagnostic kit may be displayed. FIG. 7(a) illustrates an analysis result of a positive sample and FIG. 7(b) illustrates the analysis result of a negative sample. Positive/negative may be judged at a ratio of the Raman signals of the control line and the test line.

The Raman analysis execution unit 120 analyzes the Raman signal amplified through composite nanoparticles such as gold and silver nanoparticles and composite nanoparticles such as gold (core)-silver (shell) and then amplifies a signal once more by using a silver structure to perform high-sensitivity quantitative analysis. In this case, the Raman analysis execution unit 120 detects the antigen with high sensitivity by fixing the aptamer of the diagnostic reagent to the nanoparticles for selective detection of the antigen.

When the antigen is detected according to the Raman signal detection result of the Raman analysis execution unit 120, the disease analysis unit 130 determines the type of antigen and illness corresponding to the antigen. The illness analysis unit 130 decides what illness is detected based on the aptamer based diagnostic reagent used in the process of detecting the antigen through the Raman analysis execution unit 120.

The output unit 140 may output and provide the type of detected illness to a user and include at least one of a display unit for providing the type to a visual means or a speaker for providing the type to an auditory means.

The communication unit 150 may perform communication while transmitting and receiving data to and from an external device or a server of the diagnostic equipment 1000 and for example, the communication unit 150 may transmit information on the type of detected illness together with personal information of a testee to a hospital server or a server of a diagnostic agency and transmit the information to a portable terminal of a doctor to allow an application installed in the portable terminal to verify the information.

The memory 160 stores various data such as programs, algorithms, and software used in the diagnostic equipment 1000 as well as storing data and values generated in the diagnostic equipment 1000. The memory 160 may be implemented in hardware in the diagnostic equipment 1000 or implemented in the form of an external cloud server.

The power supply unit 170 supplies power for operating the diagnostic equipment 1000. The power supply unit 170 may receive external power through a wire, but when the diagnostic equipment 1000 is implemented to be portable, the power supply unit 170 may be implemented in the form of a rechargeable battery.

The control unit 180 controls an organic connection relationship among components included in the diagnostic equipment 1000 to control the diagnostic equipment 1000 to operate according to a function and a purpose thereof.

The diagnostic equipment 1000 may rapidly analyze the acute febrile illness infected by the testee on the point through the components and even a non-specialist may analyze the illness with high accuracy and sensitivity, thereby guaranteeing even the accessibility. Further, the diagnostic equipment 1000 is miniaturized and implemented so as to be portable to be implemented in a further improved point application.

Figure 4:
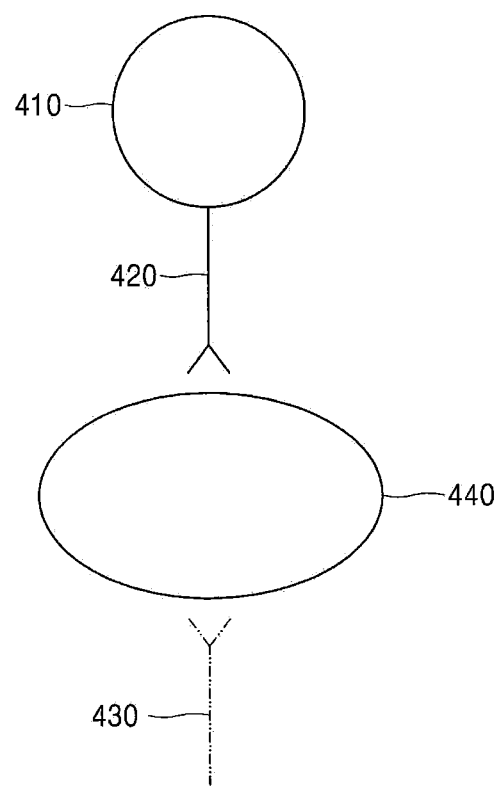
FIG. 4 is a diagram for describing a diagnostic reagent of a point-of-care system according to a proposed embodiment.

FIG. 4 is a diagram for describing a diagnostic reagent of a point-of-care system according to a proposed embodiment. As described above, the aptamer based diagnostic reagent binds with high specificity and affinity to the antigen, allowing direct detection of the antigen even without the antibody.

As described with an illustrated example, when a diagnostic reagent including an antigen detecting aptamer 420 and a fixed aptamer 430 is injected, the diagnostic reagent binds with an antigen 440 in the blood, and as a result, a nano probe 410 directly detects the antigen 440. In general, as compared with indirect detection of existence of the antigen through detection of the antibody, when the proposed aptamer based diagnostic reagent is used, a target antigen may be directly detected without waiting for generation of the antibody, thereby significantly reducing the diagnosis time. An autumn illness may be accurately and rapidly analyzed and diagnosed as compared with the related art through the rapidity, and as a result, a diagnostic system specialized to the point-of-care test (POCT) may be implemented.

Figure 5:
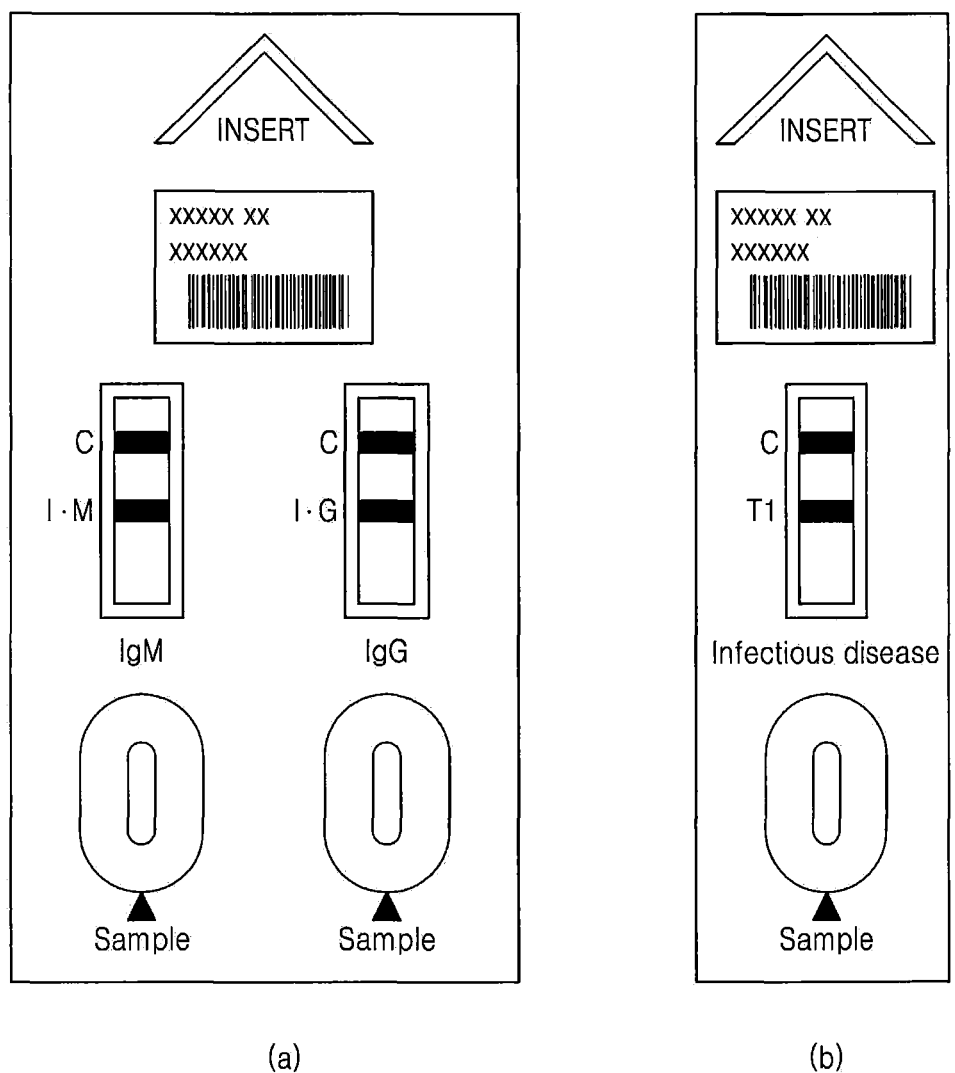
FIG. 5 is a diagram for describing a diagnostic kit of a point-of-care system according to a proposed embodiment.

FIG. 5 is a diagram for describing a diagnostic kit of a point-of-care system according to a proposed embodiment. FIG. 5(a) illustrated illustrates a diagnostic kit for antibody detection and FIG. 5(b) illustrates a diagnostic kit for antigen detection. The antibody detecting diagnostic kit is divided into two parts so as to detect both an IgM antibody and an IgG antibody and the antigen detecting diagnostic kit is configured singly.

Since the diagnostic equipment needs to operate regardless of the type of diagnostic kit, the diagnostic kit seating unit of the diagnostic equipment described above is configured to distinguish and detect two different types of diagnostic kits. For example, the diagnostic kit seating unit may separately include a portion where the antibody detecting diagnostic kit is seated and a portion where the antigen detecting diagnostic kit is seated, and both two different diagnostic kits may be seated on one seating unit.

Figure 6:
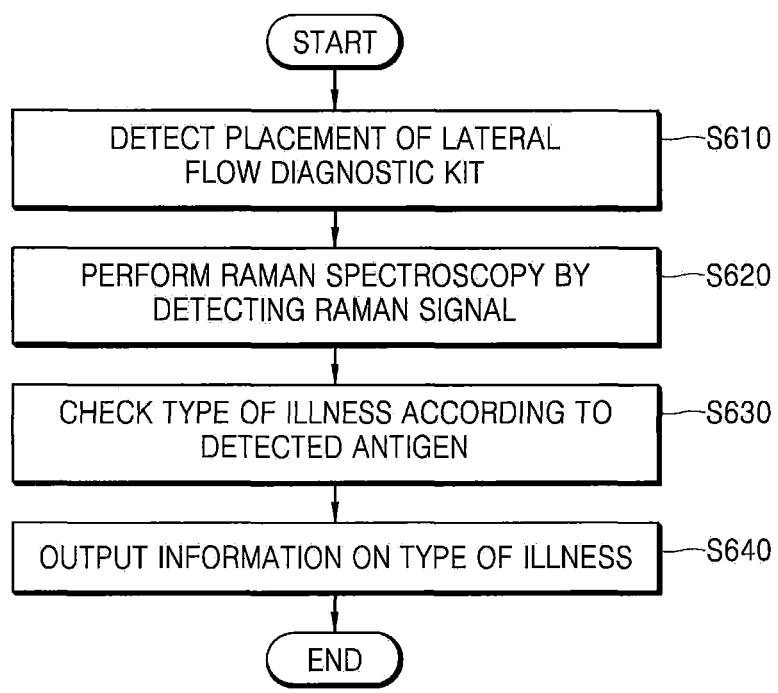
FIG. 6 is a flowchart illustrating a point-of-care method according to a proposed embodiment.

FIG. 6 is a flowchart illustrating a point-of-care method according to a proposed embodiment. In FIG. 6, the embodiments illustrated in FIGS. 2 to 5 above are shown according to a time series flow. Accordingly, even though detailed contents are omitted in FIG. 6, the contents described above may be applied in the same or similar manner.

First, the diagnostic equipment of the point-of-care system detects that the lateral flow diagnostic kit is placed (S610). The placed diagnostic kit may be at least one of the antibody detecting diagnostic kit and the antigen detecting diagnostic kit. Next, the diagnostic equipment reacts the blood injected into the diagnostic kit and the aptamer based diagnostic reagent to detect the Raman signal and performs Raman spectroscopic based analysis according to the Raman signal (S620). Through such a process, the nanoparticle and Surface Enhanced Raman Scattering (SERS) technique for amplifying the Raman signal may be used.

The diagnostic equipment detects the antigen from the blood injected into the diagnostic kit and verifies the type of illness according to the antigen (S630). Alternatively, when the Raman signal is detected as a result of Raman analysis, the diagnostic equipment may identify the type of illness based on the type of diagnostic reagent used for detection of the antigen. When the type of illness is determined, the diagnostic equipment outputs the identified information to provide what type of illness infected by the testee is to the user (S640).

Meanwhile, the point-of-care method described above may be prepared by a computer executable program and implemented by a universal digital computer which operates the program by using a computer readable medium. Further, the structure of the data used in the aforementioned method may be recorded in the computer readable medium through various means. Recording media that record executable computer programs or codes for carrying out various methods of the present invention should not be understood to include transient objects such as carrier waves or signals. The computer readable medium includes storage media such as magnetic storage media (e.g., a ROM, a floppy disk, a hard disk, and the like) and optical reading media (e.g., a CD-ROM, a DVD, and the like).

The aforementioned description of the present invention is used for exemplification, and it can be understood by those skilled in the art that the present invention can be easily modified in other detailed forms without changing the technical spirit or requisite features of the present invention. Therefore, it should be appreciated that the aforementioned embodiments are illustrative in all aspects and are not restricted. For example, respective constituent elements described as single types can be distributed and implemented, and similarly, constituent elements described to be distributed can also be implemented in a coupled form.

The scope of the present invention is represented by claims to be described below rather than the detailed description, and it is to be interpreted that the meaning and scope of the claims and all the changes or modified forms derived from the equivalents thereof come within the scope of the present invention.

What is claimed is:

1. A point-of-care system for discriminating a plurality of acute febrile illnesses, comprising:
   a diagnostic reagent detecting target antigens based on an aptamer;
   a diagnostic instrument detecting a Raman signal through a Raman analysis technique; and
   a diagnostic kit seated on a portion of the diagnostic instrument and operated based on a lateral flow method,
   wherein the diagnostic instrument includes
   a diagnostic kit seating unit configured to detect whether the diagnostic kit is placed in the diagnostic instrument and to distinguish between two different types of diagnostic kits,
   a Raman analysis execution unit reacting a blood injected into the diagnostic kit and the diagnostic reagent to each other when the diagnostic kit is placed and amplifying and detecting a generated Raman signal,
   an illness analysis unit analyzing the type of acute febrile illness infected by a subject according to the detected Raman signal by determining a type of antigen and a type of illness corresponding to the antigen, and
   an output unit outputting information on the analyzed illness.

2. The point-of-care system of claim 1, wherein the diagnostic reagent includes aptamer for antigen detection and fixed aptamer and directly detects antigen in the blood injected into the diagnostic kit.

3. The point-of-care system of claim 1, wherein the diagnostic kit seating unit includes at least one of a pressure sensor or an optical sensor.

4. The point-of-care system of claim 1, wherein the Raman analysis execution unit amplifies and detects the Raman signal by using a Surface Enhanced Raman Scattering (SERS) technique and gold-silver nanoparticles.

5. The point-of-care system of claim 1, wherein the output unit includes a display for visually providing information on the illness and a speaker for audibly providing the information.

6. A point-of-care method using a system constituted by are aptamer-based diagnostic reagent, a diagnostic instrument, and a diagnostic kit for discriminating a plurality of acute febrile illnesses, comprising:
   detecting, by the diagnostic instrument detecting a Raman signal through a Raman analysis technique, that the diagnostic kit operated by a lateral flow method is placed in the diagnostic instrument, and distinguishing between two different types of diagnostic kits;
   when it is detected whether the diagnostic kit is placed, detecting the Raman signal generated by reacting a blood injected into the diagnostic kit and a aptamer-based diagnostic reagent;
   detecting an antigen through an analysis process of the Raman signal;
   checking the type of acute febrile illness infected by a subject according to the detected antigen; and
   outputting information on the analyzed illness.

7. The point-of-care method of claim 6, wherein the diagnostic reagent includes aptamer for antigen detection and fixed aptamer and directly detects antigen in the blood injected into the diagnostic kit.

8. The point-of-care method of claim 6, further comprising detecting that the diagnostic kit is placed by at least one of a pressure sensor or an optical sensor.

9. The point-of-care method of claim 6, further comprising amplifying and detecting the Raman signal by using a Surface Enhanced Raman Scattering (SERS) technique and gold-silver nanoparticles.

10. The point-of-care system of claim 6, further comprising displaying information on the illness or audibly providing the information on the illness with a speaker.

11. The point-of-care system of claim 1, wherein the diagnostic kit seating unit is configured to distinguish and detect two different types of diagnostic kits by including a first portion where the antibody detecting diagnostic kit is seated, and a second portion where the antigen detecting diagnostic kit is seated.

12. The point-of-care method of claim 6, further comprising distinguishing and detecting two different types of diagnostic kits with a diagnostic kit seating unit comprising a first portion where the antibody detecting diagnostic kit is seated, and a second portion where the antigen detecting diagnostic kit is seated.

* * * * *